United States Patent
Mueller et al.

(10) Patent No.: US 11,866,323 B2
(45) Date of Patent: Jan. 9, 2024

(54) METHOD FOR MANUFACTURING AT LEAST ONE MEMBRANE SYSTEM, MEMBRANE SYSTEM FOR A MICROMECHANICAL SENSOR, AND COMPONENT

(71) Applicant: Robert Bosch GmbH, Stuttgart (DE)

(72) Inventors: Renate Mueller, Reutlingen (DE); Tobias Sebastian Frey, Ludwigsburg (DE)

(73) Assignee: ROBERT BOSCH GMBH, Stuttgart (DE)

( * ) Notice: Subject to any disclaimer, the term of this patent is extended or adjusted under 35 U.S.C. 154(b) by 570 days.

(21) Appl. No.: 17/053,253

(22) PCT Filed: May 7, 2019

(86) PCT No.: PCT/EP2019/061608
§ 371 (c)(1),
(2) Date: Nov. 5, 2020

(87) PCT Pub. No.: WO2019/219438
PCT Pub. Date: Nov. 21, 2019

(65) Prior Publication Data
US 2021/0238031 A1 Aug. 5, 2021

(30) Foreign Application Priority Data
May 17, 2018 (DE) .................. 10 2018 207 689.8

(51) Int. Cl.
*G01N 27/18* (2006.01)
*B81C 1/00* (2006.01)

(52) U.S. Cl.
CPC ......... *B81C 1/00182* (2013.01); *G01N 27/18* (2013.01); *B81B 2201/0214* (2013.01);
(Continued)

(58) Field of Classification Search
CPC ......... B81C 1/00182; B81C 2201/0115; B81C 2201/019; G01N 27/18; G01N 33/005; B81B 2201/0214; B81B 2203/0127
See application file for complete search history.

(56) References Cited

U.S. PATENT DOCUMENTS 6,634,213 B1 * 10/2003 O'Connor ............ G01N 33/005
73/23.31
6,840,103 B2 * 1/2005 Lee ...................... H05B 6/6458
338/35
(Continued)

FOREIGN PATENT DOCUMENTS

DE 102005023110 A 12/2005
DE 102014224063 B3 3/2016
(Continued)

OTHER PUBLICATIONS

Machine translation of JP09119913 (Year: 1989).*
(Continued)

*Primary Examiner* — David J Bolduc
(74) *Attorney, Agent, or Firm* — NORTON ROSE FULBRIGHT US LLP; Gerard A. Messina

(57) ABSTRACT

A method for manufacturing at least one membrane system for a micromechanical sensor for the calorimetric detection of gases. A wafer-shaped substrate is provided. At least one reference volume is introduced from a front side into the wafer-shaped substrate with the aid of a surface or volume micromechanical process while forming a reference membrane covering the reference volume at least in some areas. At least one measuring volume, which is adjacent to the at least one reference volume, is introduced into the substrate from a back side or the front side of the wafer-shaped substrate while forming a measuring membrane. A wafer-shaped cap substrate is applied onto the front side of the
(Continued)

wafer-shaped substrate. A membrane system and a component are described.

17 Claims, 2 Drawing Sheets

(52) U.S. Cl.
CPC . *B81B 2203/0127* (2013.01); *B81C 2201/019* (2013.01); *B81C 2201/0115* (2013.01)

(56) References Cited

U.S. PATENT DOCUMENTS

| | | | | |
|---|---|---|---|---|
| 2002/0170875 | A1* | 11/2002 | Benzel | B81C 1/00047 216/2 |
| 2005/0006236 | A1* | 1/2005 | Kim | G01N 27/18 204/415 |
| 2005/0025215 | A1* | 2/2005 | Arndt | G01N 25/18 374/44 |
| 2005/0265422 | A1* | 12/2005 | Bonne | G01P 15/008 374/44 |
| 2006/0057816 | A1* | 3/2006 | Benzel | G01P 15/0802 438/424 |
| 2008/0153174 | A1* | 6/2008 | Galloway | G01N 33/005 436/144 |
| 2008/0154432 | A1* | 6/2008 | Galloway | G01N 33/005 700/271 |
| 2008/0154433 | A1* | 6/2008 | Galloway | G01N 33/005 700/271 |
| 2009/0017551 | A1* | 1/2009 | Kesper | G01N 25/28 436/144 |
| 2009/0129440 | A1* | 5/2009 | Opitz | G01N 27/14 374/178 |
| 2010/0084333 | A1* | 4/2010 | Hoogerwerf | B01D 67/0062 977/891 |
| 2010/0164027 | A1* | 7/2010 | Kramer | G01L 19/0038 257/419 |
| 2011/0147864 | A1* | 6/2011 | Kramer | G01L 9/0042 257/419 |
| 2011/0308324 | A1* | 12/2011 | Gamage | G01L 9/0054 29/25.35 |
| 2011/0316100 | A1* | 12/2011 | Kim | B81C 1/00158 257/E21.09 |
| 2012/0042712 | A1* | 2/2012 | Kishi | G01N 27/18 73/23.35 |
| 2012/0272728 | A1* | 11/2012 | Fukui | G01N 33/005 73/335.05 |
| 2012/0297860 | A1 | 11/2012 | Izawa et al. | |
| 2015/0268115 | A1* | 9/2015 | Robert | G01L 13/025 73/718 |
| 2019/0033242 | A1* | 1/2019 | Motta | G01N 27/123 |
| 2019/0041347 | A1* | 2/2019 | Matsukura | G01N 27/4077 |
| 2019/0086351 | A1* | 3/2019 | Yamashita | G01N 33/005 |
| 2019/0234821 | A1* | 8/2019 | Besling | B81B 7/0061 |
| 2019/0265119 | A1* | 8/2019 | Siegert | G01L 19/147 |
| 2020/0348252 | A1* | 11/2020 | Mueller | G01N 33/0027 |
| 2021/0148845 | A1* | 5/2021 | König | B81B 7/0029 |

FOREIGN PATENT DOCUMENTS

| | | |
|---|---|---|
| DE | 102016200270 A1 | 7/2017 |
| EP | 1775259 A1 | 4/2007 |
| JP | H0196549 A | 4/1989 |
| JP | H09119913 A | 5/1997 |
| JP | 2012063351 A | 3/2012 |

OTHER PUBLICATIONS

International Search Report for PCT/EP2019/061608, dated Aug. 6, 2019.

Li Wang et al., "A MEMS Nanocalorimeter for Biomolecular Characterization," Nano/Micro Engineered and Molecular Systems, 2006 NEMS '06, 1ST IEEE International Conference ON, IEEE, 2006, pp. 349-352.

Bin Wang et al. "A MEMS Differential-Scanning-Calorimetric Sensor for Thermodynamic Characterization of Biomolecules," Journal of Microelectromechanical Systems, IEEE Service Center, vol. 21, No. 5, 2012, pp. 1165-1171.

* cited by examiner

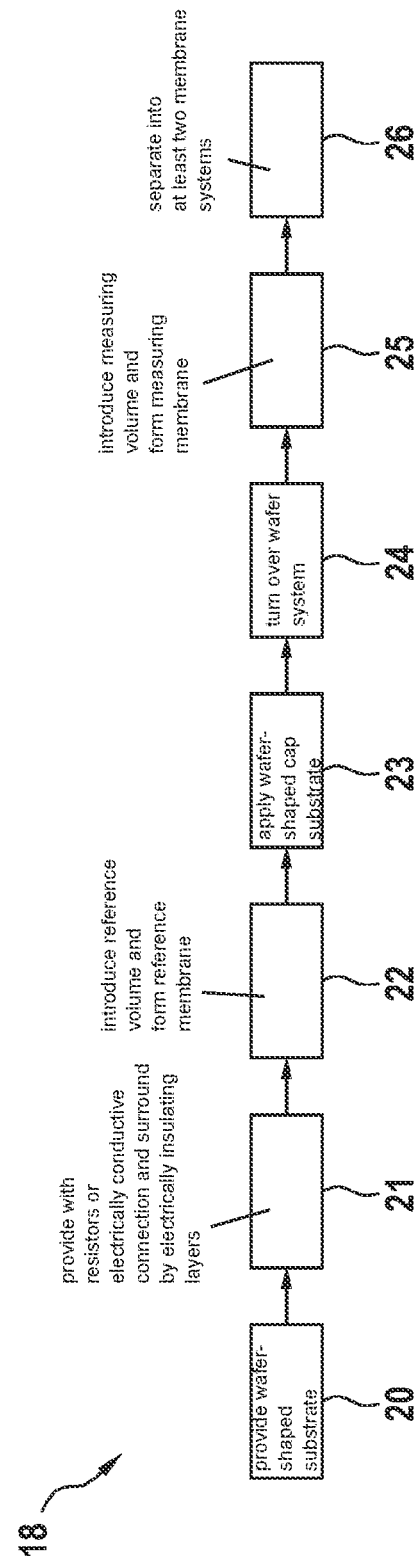

METHOD FOR MANUFACTURING AT LEAST ONE MEMBRANE SYSTEM, MEMBRANE SYSTEM FOR A MICROMECHANICAL SENSOR, AND COMPONENT

FIELD

The present invention relates to a method for manufacturing at least one membrane system for a micromechanical sensor for the calorimetric detection of gases and to a membrane system and a component including a membrane system of this type.

BACKGROUND INFORMATION

Sensors based on the calorimetric principle may be utilized for a detection of hydrogen. Sensors of this type are usually made up of a membrane, on which a heating element is situated. This heating element may be operated with the aid of a constant current/voltage or with the aid of a constant power by way of a control electronics system. As a result, an excessive temperature as compared to the ambient temperature is implemented. The mode of operation of sensors of this type is based on the thermal conductivity of hydrogen, which, at 1810 µW/cmK, is higher than the thermal conductivity of air, which has a value of 260 µW/cmK.

If hydrogen is located in the surroundings of the heating element, the temperature of the heating element decreases due to the higher thermal conductivity of the hydrogen and the associated greater heat dissipation. The resistance of the heating element decreases. This change in resistance results in an additional heat output, which must be applied by the control electronics system in order to hold the heating element at a constant temperature. The additional heat output is proportional to the concentration of the hydrogen.

Since the thermal conductivity depends on the ambient temperature, the ambient temperature may be measured with the aid of a further temperature sensor, for example, with the aid of a further platinum resistor in an adjacent area of the membrane.

The atmospheric humidity in the surroundings of the membrane is also relevant with respect to the consideration of the thermal conductivity of the air and must be taken into account with the aid of additional sensors or a more complex evaluation of the measured data.

Due to the large number of factors to be taken into account, a configuration of the control electronics system is made difficult, since a large measuring range and many variables are to be taken into account. In parallel thereto, a high resolution and accuracy of the hydrogen detection is necessary, however.

In addition to the utilization of a Wheatstone bridge to filter out the ambient effects, the operating voltage may also be varied, in order to be able to differentiate hydrogen from an atmospheric humidity. This differentiation is necessary, in particular, when hydrogen is to be detected in the exhaust air of a fuel cell stack, for example, but not necessarily, the fuel cell stack of a fuel cell vehicle. A high atmospheric humidity prevails there.

SUMMARY

An object underlying the present invention is to provide a manufacturing method and an improved membrane system, which reduce external effects on a concentration measurement.

This object is achieved, according to example embodiments of the present invention. Advantageous embodiments and refinements of the present invention are described herein.

According to one aspect of the present invention, a method is provided for manufacturing at least one membrane system for a micromechanical sensor for the calorimetric detection of gases.

In accordance with an example embodiment of the present invention, in a method step of the approach according to the present invention, a wafer-shaped substrate is provided. The wafer-shaped substrate may preferably be a doped semiconductor or an undoped semiconductor.

A thermally and electrically insulating coating of, for example, oxide, nitride, oxide-nitrite, or oxide-nitrite-oxide, or the like, may preferably be applied onto the wafer-shaped substrate. The thermally and electrically insulating layer subsequently ideally forms an etch-stop layer. Advantageously, the material is selected in such a way that atmospheric humidity may not be intercalated into the layer or does not diffuse through the layer.

The wafer-shaped substrate preferably already encompasses electrically conductive structures for forming heating elements, for example, made up of platinum, aluminum, molybdenum, tungsten, copper, gold, silver, doped silicon, or the like, with or without adhesion-promoter layers made up of aluminum, titanium, tantalum, or their oxides or nitrides, and the like. These may be, for example, equipped, sputtered, or vapor-deposited thereon; a combination of these steps is also possible. Moreover, the wafer-shaped substrate includes a further electrical insulation via the metallization, for example, made up of oxide or nitride, or the like. A further function of the insulation layer is the protection against or the separation from ambient effects such as dust and moisture.

In the method according to the example embodiment of the present invention, at least one reference volume is introduced from a front side of the wafer-shaped substrate into the wafer-shaped substrate with the aid of a surface micromechanical and/or a volume micromechanical process while forming a reference membrane covering the reference volume at least in some areas.

This may be achieved, for example, with the aid of wet etching or sacrificial layer etching.

Alternatively or additionally to this method step, at least one reference volume may be introduced into the wafer-shaped substrate from a front side while forming a reference membrane covering the reference volume at least in some areas, with the aid of a PorSi process with or without subsequent removal of the porous silicon with the aid, for example, of a dry etching step or a cloud trench etching process.

Alternatively, only one process may be utilized or a combination of the individual processes.

The reference volume may be utilized as a reference for the gas measurement, for example, during the utilization of a Wheatstone measuring bridge in the metal layer.

The reference volume may be designed to be open or closed in the direction of one of the two surfaces of the wafer-shaped substrate; in the open design, an exchange with gases and/or gas mixtures in the surroundings is possible. In the closed variant, certain gases and/or gas mixtures may be enclosed in the reference volume.

In one further method step, at least one measuring volume adjacent to the at least one reference volume is introduced into the wafer-shaped substrate from a back side or the front side of the wafer-shaped substrate while forming a measuring membrane.

The measuring volume, as well as the reference volume, may be introduced into the wafer-shaped substrate with the aid of a suitable surface micromechanical process. In addition, a volume micromechanical process made up of an anisotropic etching method or an isotropic etching method and/or a combination of an anisotropic etching method and an isotropic etching method may also be utilized. This may be carried out, for example, with the aid of sacrificial layer etching and/or wet etching.

Alternatively or additionally, at least one measuring volume may be introduced into the wafer-shaped substrate from a front side while forming a measuring membrane covering the measuring volume at least in some areas, and an initially closed measuring volume, with the aid of a PorSi process with or without subsequent removal of the porous silicon.

One further possible process control is a surface micromechanical and/or a volume micromechanical and PorSi process acting from the front side of the wafer-shaped substrate for simultaneously generating the reference volume and the measuring volume. This approach has the advantage of a shortened process control, and a volume micromechanical process acting from the back side is possible for the gas-conducting opening of the measuring volume. In this specific embodiment, the wafer-shaped cap substrate, which is defined more precisely further below, could be dispensed with overall. This is possible, for example, in the case of wet etching processes and results in a very favorable way to manufacture the wafer system, because material costs and the manufacturing time of the sensor may be further reduced.

During the manufacture of a reference or measuring volume or a reference or measuring cavity, a membrane delimiting the volume may be formed at the same time. One advantage of an embodiment as a membrane, such as a reference membrane and/or a measuring membrane, is that an excessive temperature with respect to the surroundings may be set in combination with a minimized power consumption.

Due to the membrane system and the electrical configuration as a Wheatstone bridge, a sensor signal may be hardly affected by the changing environmental conditions, such as temperature and atmospheric humidity, as well as aging of the chip and an associated drift of the sensor.

In a further method step, a wafer-shaped cap substrate is applied onto the front side of the wafer-shaped substrate. The advantage of an application of the wafer-shaped cap substrate onto the front side of the wafer-shaped substrate is the increase of the mechanical stability and the mechanical strength. The wafer-shaped cap substrate implements a fixed thermal boundary condition; therefore, the adjustability and reproducibility of the system are increased. In a closed specific embodiment of the wafer-shaped cap substrate, a further cavity may be implemented above the membrane, which is filled, for example, with a thermally differently conducting gas. In particular in the case of a poorly conducting gas or vacuum, the sensitivity of the provided measuring device is increased.

Based on the described method steps, a simplified manufacturing method may be implemented for a micromechanical sensor, in particular for a double-membrane chip including an enclosed reference volume for the detection of gases, in particular for hydrogen, in particular with the aid of the principle of the thermal conductivity in gases and/or gas mixtures, convection or radiation.

In one further specific embodiment according to the present invention, a duct structure may be formed in the wafer-shaped cap substrate for the targeted supply of measuring gas and reference gas.

Thereafter, the wafer may be separated into a plurality of wafer sections. The particular wafer sections may be utilized for a manufacture of the sensors.

According to one specific embodiment of the method, the wafer-shaped cap substrate is applied onto the wafer-shaped substrate after the introduction of the reference volume. As a result, the measuring volume, similarly to the reference volume, may be introduced into the wafer-shaped substrate with the aid of a surface micromechanical and a volume micromechanical process or a PorSi process acting from the front side of the wafer-shaped substrate. Thereafter, the wafer-shaped cap substrate may be placed on the processed wafer-shaped substrate.

Due to this particularly favorable and simplified processability of the method according to the present invention, for example, the face down processing for the manufacture and/or the gas-conducting opening of the measuring volume with the aid of a trench etching process may be implemented. A direct contact of the front side of the wafer with a holding device, which is referred to in the following as a chuck, (this is referred to as face down processing) may result in damage of the reference membrane and/or breakage of the membrane during the processing due to unevenness and particles on the holding device.

According to one further specific embodiment of the method according to the present invention, the wafer-shaped cap substrate is applied onto the wafer-shaped substrate after the introduction of the at least one measuring volume.

This has the advantage that the joint and the wafer-shaped cap substrate are not damaged in the case, for example, of wet etching methods.

According to one further specific method of the method according to the present invention, the at least one measuring volume is introduced into the wafer-shaped substrate with the aid of dry etching. One advantage of the dry etching method is that previously applied sacrificial structures may be removed in a defined manner. Therefore, undercuts may be generated, which may bring, for example, fluid dynamics-related advantages during the introduction of the gas to be measured.

Alternatively and/or additionally, the at least one measuring volume is introduced into the wafer-shaped substrate with the aid of a trench etching process. One advantage of the manufacturing process with the aid of trench etching is the introduction of arbitrary geometries. Therefore, small chips may be implemented.

Alternatively and/or additionally, the at least one measuring volume is introduced into the wafer-shaped substrate with the aid of a wet-chemical etching method. In this case, the wafer-shaped substrate does not rest on a chuck and, therefore, this step may take place before the cap has been applied. If further mechanical stability or an increased stability of the wafer-shaped substrate is not necessary, the cap may be dispensed with.

One further advantage of the wet-chemical etching method is that the front side and the back side of the wafer-shaped substrate may be done in one simultaneous work step. Therefore, processing may be carried out very cost-effectively with a high level of process homogeneity.

The at least one measuring volume may therefore be flexibly introduced into the wafer-shaped substrate by removal of material with the aid of a plurality of different manufacturing methods.

According to one further specific embodiment of the method according to the present invention, the wafer-shaped cap substrate is applied onto the front side of the wafer-shaped substrate with the aid of adhesive bonding, soldering, wafer bonding, or welding, where wafer bonding is to be understood to be a glass frit bonding, a eutectic bond or an anodic bond. Different bonding methods allow for another process control, in particular on a present boundary layer of wafer-shaped substrate and wafer-shaped cap substrate. Moreover, different bonding methods have a different media resistance in combination with an implementable structure width.

Alternatively, an adhesive bonding step may also be carried out after the soldering, bonding, or welding of the wafer-shaped cap substrate. This may be utilized for the additional fixation of the wafer-shaped cap substrate or the sealing of the membrane system.

The wafer-shaped cap substrate may therefore be flexibly situated on the wafer-shaped substrate with the aid of different methods.

According to one further specific embodiment of the method according to the present invention, at least one reference volume, which is open or closed in the direction of the front side of the wafer-shaped cap substrate, is formed between the at least one reference membrane and the wafer-shaped cap substrate and/or between the at least one measuring membrane and the wafer-shaped cap substrate during an application of the wafer-shaped cap substrate onto the wafer-shaped substrate. For this purpose, the wafer-shaped cap substrate may include recesses, which have been introduced in advance, in the area of the at least one reference membrane and/or in the area of the at least one measuring membrane. These recesses may extend through a thickness of the wafer-shaped cap substrate and, therefore, form a gas passage through the wafer-shaped cap substrate.

Alternatively or additionally, the wafer-shaped cap substrate may form additional volumes over the membranes, which may be filled, for example, with a reference gas.

According to one further specific embodiment of the method according to the present invention, the at least one measuring volume, introduced into the wafer-shaped substrate from the front side of the wafer-shaped substrate while forming the measuring membrane, is opened, in a gas-conducting manner, from the back side of the wafer-shaped substrate. The measuring volume may have been introduced in the wafer-shaped substrate so as to be open on the back side or may have been designed to be gas-conducting with the aid of openings additionally introduced into the wafer-shaped substrate.

The advantage of an introduction of a reference volume from the front side and of the measuring volume from the back side is that different gases may be supplied from the front side and the back side. It is possible, for example, to supply air from the front side and hydrogen from the back side.

For example, ducts and openings may be introduced into the back-side wall of the at least one measuring volume with the aid of trench etching processes. The dimension of the openings is pronounced in such a way, in this case, that gaseous media may enter the at least one measuring volume. Particles and aerosols do not enter the at least one measuring volume through the connection, due to their particle size.

Alternatively, the at least one measuring volume may be very cost-effectively opened with the aid of a wet-chemical process.

Due to the type of the process control according to the present invention for generating the reference volume from the front side of the wafer-shaped substrate, a seal of the reference volume in the direction of a back side of the wafer-shaped substrate may be dispensed with, since a closed reference volume arises, which does not need to be additionally closed with the aid, for example, of a separate base wafer.

According to one further specific embodiment of the method according to the present invention, the at least one measuring volume is opened on the back side in a gas-conducting manner with the aid of an etching process applied onto the back side of the wafer-shaped substrate. This etching process may be a trench etching process, a dry etching process, a wet etching process and/or a combination of the steps, or the like. The at least one measuring volume introduced in the wafer-shaped substrate and/or the reference volume may be modified in a gas-conducting manner in the direction of the back side of the wafer-shaped substrate with the aid of a porous semiconductor technology, such as PorSi technology.

The reference volume may be opened only from the front side of the system in the same way as the measuring volume. This would have the advantage that the Wheatstone bridge is more easily matchable to the measuring volume due to greater symmetry.

One advantage of a porous semiconductor structure in the at least one measuring volume is that the semiconductor structure has a large surface with adjustable pore sizes and, therefore, may perform a filter function with respect to other gases and/or particles. The porous structure is pronounced in such a way that particles, aerosols, or atmospheric humidity may not enter the at least one measuring volume due to the particle size. In a process control including PorSi, a porous semiconductor structure is applied anyway and the open porosity may be adjusted with the aid of the process control.

According to one further specific embodiment of the method according to the present invention, a sealant is situated on the back side of the wafer-shaped substrate. The cross section of the back side of the wafer-shaped substrate to be sealed may be reduced with the aid of the gas-conducting supply to the measuring volume, so that a seal against moisture and other environmental influences may be carried out in a technically simple way with the aid of wide sealing rings, which are utilized, for example, for a media resistance, in the area of the at least one measuring volume.

One advantage of the installed sealant is that the gas located underneath the measuring volume, for example, a hydrogen-moisture mixture, may be separated, in an exhaust air duct, from a second gas, which is located above the wafer-shaped substrate, such as ambient air. One particular advantage is that, as a result, the bonding pads and bonding wires may be separated from a gas damaging to these or from any other component of the air (moisture). The sealant is seated, in particular, on the back side, since the dielectric layers present there are particularly stable with respect to moisture. It is also possible to situate the sealant on the front side when other sealing functions are involved, for example, with respect to dust.

According to one further specific embodiment of the method according to the present invention, at least one resistor and at least one electrically conductive connection are placed onto the at least one reference membrane and the at least one measuring membrane, the wafer-shaped substrate connected to the wafer-shaped cap substrate being separated into at least two membrane systems. In particular, as a result, a Wheatstone bridge circuit may be applied onto the membrane system ahead of a separation step. As a result, a plurality of membrane systems may be simultaneously processed or manufactured in a technically simple way.

The implementation of the bridge circuit may take place on a single chip in the specific embodiment of at least one double membrane or on a chip including a membrane, in the case of which the cap provides measuring and reference volumes and separates these from one another. The sensor signal of a sensor of this type may not be changed by changing environmental conditions or an aging of the chip or the utilized metals and an associated drift of the resistance, since all resistors of the bridge circuit are subjected to the same fluctuations and, therefore, the bridge voltage does not change.

Moreover, production-related fluctuations in the resistors mounted onto the membrane system may affect a performance of the sensor, since the resistors of the bridge circuit are situated in close proximity to one another and, therefore, are subjected to these fluctuations to the same extent. When all resistors in a bridge circuit undergo the same fluctuations, this has little effect on a resultant bridge voltage.

According to one further specific embodiment of the method according to the present invention, at least one reference volume is introduced into the wafer-shaped substrate from a front side while forming a reference membrane covering the reference volume at least in some areas, with the aid of a PorSi process with or without subsequent removal of the porous silicon.

Moreover, according to one specific embodiment of the method according to the present invention, at least one reference volume is introduced into the wafer-shaped substrate from a front side while forming a reference membrane covering the reference volume at least in some areas, and an initially closed measuring volume is introduced into the wafer-shaped substrate from a front side while forming a measuring membrane covering the measuring volume at least in some areas, with the aid of a PorSi process with or without subsequent removal of the porous silicon.

In the case of the process control with the aid of PorSi, the reference volume and the measuring volume may be introduced simultaneously or individually. Thereafter, it is possible to open these cavities toward the top side and/or the back side, depending on the desired subsequent application.

In the case of a process control with the aid of PorSi, the wafer-shaped cap substrate may be dispensed with, which further streamlines the process flow. Moreover, the stability of the reference membrane and/or the measuring membrane may be increased, in that it is supported by a porous structure; as a result, measurements may be carried out at higher pressures in the reference volume and/or the measuring volume.

One advantage of the process control with the aid of the PorSi process is that a filter function may be implemented in a targeted manner with the aid of the porous silicon in at least one reference volume and/or measuring volume. The porous semiconductor structure has a large surface and pore sizes, which are adjustable with the aid of the process control, and may therefore perform a filter function with respect to undesirable particles, aerosols and/or atmospheric humidity. Undesirable components may not enter the at least one reference volume and/or measuring volume, due to the particle size. This could be particularly advantageous when the gas and/or gas mixture to be measured are/is contaminated.

According to one further aspect of the present invention, a membrane system for a sensor for the calorimetric detection of gases is provided, manufactured according to a method according to the present invention. The membrane system includes a cap substrate section connected to a substrate section and at least one reference volume, which is introduced into the substrate section and is delimited, on at least one side, by a reference membrane in the direction of the cap substrate section. Moreover, the membrane system includes at least one measuring volume, which is introduced into the substrate section and is delimited by a one-sided measuring membrane in the direction of the cap substrate section, the reference membrane preferably being opened in a fluid-conducting manner, at least in some areas, in the direction of a front side of the cap substrate section. The measuring volume is designed to be fluid-conducting in the direction of a back side of the substrate section.

A membrane system manufactured according to the method for a sensor for the calorimetric detection of gases includes at least one measuring volume encompassing a gas access from the back side of the wafer-shaped substrate and at least one reference volume, which is closed in the direction of the back side of the wafer-shaped substrate. The closed reference volume may be utilized as a reference for the gas measurement, for example, during the utilization of a Wheatstone measuring bridge in the metal layer.

The membrane system may be utilized, for example, for a design as a double-membrane chip, in the case of which a cavity or a measuring volume is open, for example, from the back side of the wafer-shaped substrate and, therefore, has a gas access, the adjacent reference volume being closed from this access side (see PA 13).

A spatial separation of the reference membrane from the measuring membrane proves to be particularly favorable, since it may form, in interaction with the electrically conductive structures, a reference resistance, in order to decouple possible changes, such as humidity and temperature and/or other changes, in the surroundings from the measuring signal.

According to one further advantage of the reference volume, a defined gas and/or gas mixture may be enclosed and, therefore, measured in relation thereto.

According to one further aspect of the present invention, a component, in particular a sensor, is provided with a membrane system according to the present invention.

The membrane system may preferably be a section of a wafer system, which was processed according to the method according to the present invention and, thereafter, separated into a plurality of sections. Due to the openings of the measuring volume and of the reference volume, which have been introduced opposite to one another, a gas flow may be guided into the particular volumes in a technically simple way. In particular, a hermetic shielding of the reference volume may be implemented with the aid of the cap substrate section. A hermetic shielding may also be implemented in that the reference volume is not opened in a gas-conducting manner or is closed again after the filling with a reference gas. As a result, external effects on a measurement, for example, a hydrogen concentration, may be reduced, whereby a control electronics system for operating the sensor based on the membrane system may be designed to be technically simpler and more cost effective.

Preferred exemplary embodiments according to the present invention are explained in greater detail in the following with reference to highly simplified schematic representations.

BRIEF DESCRIPTION OF THE DRAWINGS

FIG. 3 shows a schematic representation of a method for manufacturing a membrane system according to a first exemplary embodiment.

DETAILED DESCRIPTION OF EXAMPLE EMBODIMENTS

Figure 1:
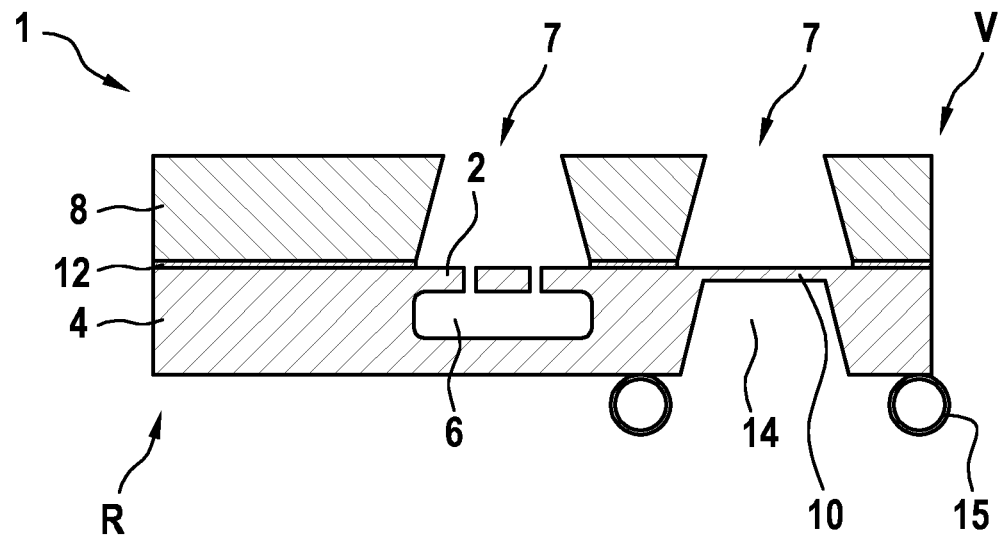
FIG. 1 shows a schematic section through a membrane system according to a first specific embodiment of the present invention.

In the figures, the same structural elements each have the same reference numerals.

FIG. 1 shows a schematic section through a membrane system 1 according to a first specific embodiment of the present invention. Membrane system 1, in this case, is a section of a wafer including a plurality of membrane systems 1, which were separated from one another with the aid of a separation process.

Membrane system 1 is designed as a system for a double-membrane chip and may be manufactured according to a manufacturing process for layers of a membrane, for example, an ONO membrane (oxide-nitride-oxide) including at least one strip conductor contained therein, for example, made up of the metal platinum, gold, silver, copper, molybdenum, or tungsten, or non-metallic, conductive layers such as polysilicon or a similar material. Alternatively, the membrane may be made up of only oxide, only nitride, or a mixture of both. System 1 encompasses a reference membrane 2, which was manufactured with the aid of a surface or volume micromechanical process or a PorSi process, the latter possibly in combination with a dry etching step for removing the porous silicon structure in a wafer-shaped substrate 4. In the process, a reference volume 6, which is delimited by reference membrane 2 in the direction of a front side V of wafer-shaped substrate 4, is brought about simultaneously. Reference membrane 2 is open at least in some areas in this case, so that a gas exchange with reference volume 6 may take place.

System 1 encompasses a wafer-shaped cap substrate 8, which was applied onto wafer-shaped substrate 4 after the manufacture of reference membrane 2. Wafer-shaped cap substrate 8 encompasses recesses 7 in the area of membranes 2, 10, which extend through wafer-shaped cap substrate 8. Areas 2 and 10 may also be connected to each other. According to the exemplary embodiment, recesses 7 include oblique edges; these may be caused by a wet etching process. Recesses 7 may also be introduced into wafer-shaped cap substrate 8 with the aid of other material-removal methods, however, such as trench etching.

Wafer-shaped cap substrate 8 is situated on wafer-shaped substrate 4 with the aid of wafer bonding utilizing glass frit. Due to wafer-shaped cap substrate 8, system 1 obtains additional stability.

Moreover, system 1 encompasses a measuring membrane 10 adjacent to reference membrane 2. Measuring membrane 10 was manufactured into wafer-shaped substrate 4 during a further processing having a so-called "face down" orientation of system 1. An etching process for generating a measuring volume 14 was used on back side R of the wafer-shaped substrate. Measuring volume 14 is designed to be open in the direction of back side R and therefore allows for an unobstructed gas flow to, but not through, measuring membrane 10. In the case of another type of etching process, which does not require face down processing, such as wet etching, or which holds system 1 at the edge, wafer-shaped cap substrate 8 may also be dispensed with, if necessary.

In the area of measuring volume 14, a sealant 15 in the form of a sealing ring 15 is situated at back side R of wafer-shaped substrate 4.

Figure 2:
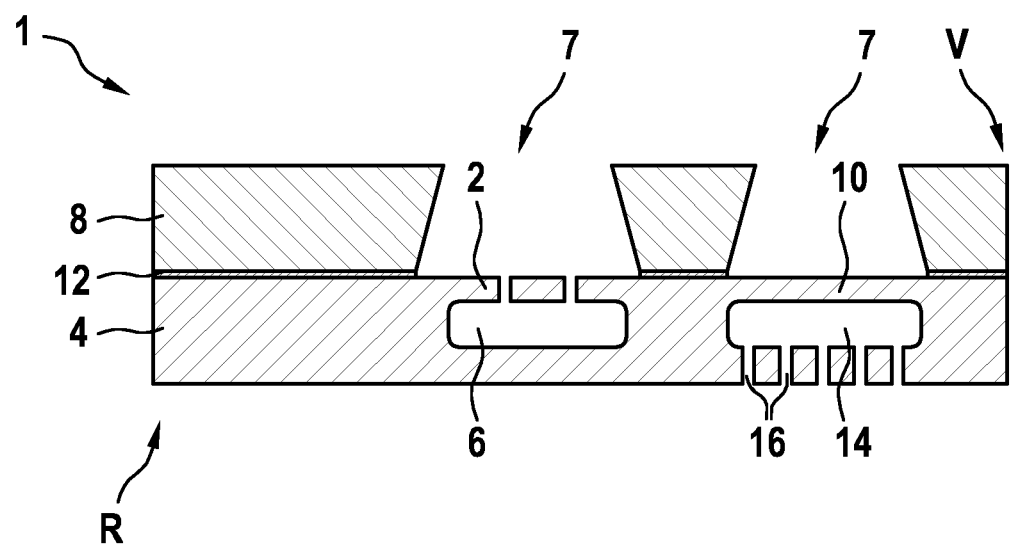
FIG. 2 shows a schematic section through a membrane system according to a second specific embodiment of the present invention.

FIG. 2 shows a schematic section through a membrane system 1 according to a second specific embodiment of the present invention. In contrast to membrane system 1 according to the first exemplary embodiment, in this case, measuring volume 14 was introduced into wafer-shaped substrate 4 from front side V of wafer-shaped substrate 4 also with the aid of a surface or volume micromechanical process or a PorSi process. A so-called cloud trench etching process may also be used in this case. Ideally, thereafter, a coating with an ONO membrane and the embedded metal structure made up of platinum is carried out. As a result, measuring volume 14 is closed toward the front side and toward back side R of wafer-shaped substrate 4 and was opened, in a gas-conducting manner, toward back side R with the aid of a subsequent step, for example, with the aid of a trench etching process or another etching process. As a result, measuring volume 14 encompasses openings 16, which are situated on the back side and preferably prevent particles and moisture from entering measuring volume 14.

FIG. 3 shows a schematic representation of a method 18 for manufacturing a membrane system 1 according to a first exemplary embodiment.

In a first method step 20, a wafer-shaped substrate 4 is provided.

Wafer-shaped substrate 4 may be subsequently equipped or provided with resistors or with electrically conductive connections in the form of one or multiple coatings and its/their structuring with the aid of lithography, and the electrically conductive layer is surrounded 21 by electrically insulating layers. The conductive connections preferably form heating resistors.

Thereafter, at least one reference volume 6 is introduced 22 from a front side V into wafer-shaped substrate 4 with the aid of a surface or volume micromechanical process or a PorSi process including a dry etching step, while forming a reference membrane 2 covering reference volume 6 at least in some areas.

Alternatively or additionally, the electric lines and enveloping electrically and thermally insulating layers may also be applied onto wafer-shaped substrate 4 according to method step 21 after formation 22 of reference volume 6 and/or measuring volume 14.

In a further step 23, a wafer-shaped cap substrate 8 is applied onto wafer-shaped substrate 4 and the wafer system is turned over 24, so that a processing of back side R may be carried out. Alternatively, this step may be dispensed with.

In one step 25, at least one measuring volume 14, which is adjacent to the at least one reference volume 6, is introduced into wafer-shaped substrate 4 from back side R of wafer-shaped substrate 4 while forming a measuring membrane 10. If measuring volume 14 has already been manufactured, a gas supply or a fluid-conducting connection to measuring volume 14 may be introduced from back side R of wafer-shaped substrate 4 in this step 25.

In a final step 26, wafer-shaped substrate 4 connected to wafer-shaped cap substrate 8 may be separated into at least two membrane systems 1.

What is claimed is:

1. A method for manufacturing at least one membrane system for a micromechanical sensor for calorimetric detection of gases, the method comprising the following steps:
providing a wafer-shaped substrate;

introducing at least one reference volume from a front side into the wafer-shaped substrate using a surface or volume micromechanical process while forming a reference membrane covering the reference volume at least in some areas;

introducing at least one measuring volume adjacent to the at least one reference volume, into the wafer-shaped substrate from a back side or the front side of the wafer-shaped substrate while forming a measuring membrane; and applying a wafer-shaped cap substrate onto the front side of the wafer-shaped substrate.

2. The method as recited in claim 1, wherein the wafer-shaped cap substrate is applied onto the wafer-shaped substrate after the introduction of the reference volume.

3. The method as recited in claim 1, wherein the wafer-shaped cap substrate is applied onto the wafer-shaped substrate after the introduction of the at least one measuring volume.

4. The method as recited in claim 1, wherein the at least one measuring volume is introduced into the wafer-shaped substrate using: (i) dry etching, or (ii) a trench etching process, or (iii) a wet etching process.

5. The method as recited in claim 1, wherein the wafer-shaped cap substrate is applied onto the front side of the wafer-shaped substrate using: (i) anodic bonding, or (ii) eutectic bonding, or (iii) bonding with using glass frit, or (iv) adhesive bonding, or (v) soldering, or (vii) welding.

6. The method as recited in claim 1, wherein the at least one reference volume, which is open or closed in A direction of the front side of the wafer-shaped cap substrate, is formed between the reference membrane and the wafer-shaped cap substrate and/or between the measuring membrane and the wafer-shaped cap substrate, during an application of the wafer-shaped cap substrate onto the wafer-shaped substrate.

7. The method as recited in claim 1, wherein the at least one measuring volume, introduced into the wafer-shaped substrate from the front side of the wafer-shaped substrate while forming the measuring membrane, is opened in a gas-conducting manner from the back side of the wafer-shaped substrate.

8. The method as recited in claim 7, wherein the at least one measuring volume is opened on the back side in a gas-conducting manner: (i) by material removal on the back side of the wafer-shaped substrate or (ii) using a porous semiconductor structure introduced on the back side of the wafer-shaped substrate.

9. The method as recited in claim 8, wherein a porous silicon structure is removed.

10. The method as recited in claim 1, wherein a sealant is situated on the back side of the wafer-shaped substrate.

11. The method as recited in claim 1, wherein at least one resistor and at least one electrically conductive connection are placed onto the reference membrane and the measuring membrane, the wafer-shaped substrate connected to the wafer-shaped cap substrate is separated into at least two membrane systems.

12. The method as recited in claim 1, wherein the at least one reference volume is introduced from the front side into the wafer-shaped substrate using a PorSi process, with or without subsequent removal of a porous silicon, while forming the reference membrane covering the reference volume at least in some areas.

13. The method as recited in claim 1, wherein the at least one reference volume is introduced into the wafer-shaped substrate from the front side while forming the reference membrane covering the reference volume at least in some areas, and an initially closed measuring volume is introduced into the wafer-shaped substrate from the front side while forming the measuring membrane covering the measuring volume at least in some areas, using a PorSi process with or without subsequent removal of the porous silicon.

14. A membrane system for a sensor for calorimetric detection of gases, comprising
a cap substrate section connected to a substrate section;
at least one reference volume introduced into the substrate section, which is delimited, on one side, by a reference membrane in a direction of the cap substrate section;
at least one measuring volume introduced into the substrate section, which is delimited, on one side, by a measuring membrane in a direction of the cap substrate section;
wherein the reference membrane is fluid-conducting, at least in some areas, in a direction of a front side of the cap substrate section, and the measuring volume is fluid-conducting in a direction of a back side of the substrate section.

15. A component, comprising:
a membrane system including:
a cap substrate section connected to a substrate section;
at least one reference volume introduced into the substrate section, which is delimited, on one side, by a reference membrane in a direction of the cap substrate section;
at least one measuring volume introduced into the substrate section, which is delimited, on one side, by a measuring membrane in a direction of the cap substrate section;
wherein the reference membrane is fluid-conducting, at least in some areas, in a direction of a front side of the cap substrate section, and the measuring volume is fluid-conducting in a direction of a back side of the substrate section.

16. The component as recited in claim 15, wherein the component is a sensor.

17. The method as recited in claim 1, wherein the at least one measuring volume is formed such that the gases enter via a plurality of openings formed on the back side.

* * * * *